(12) United States Patent
Mansfield

(10) Patent No.: US 8,551,896 B2
(45) Date of Patent: *Oct. 8, 2013

(54) TEAR RESISTANT LAMINATE

(75) Inventor: Todd Leon Mansfield, Cincinnati, OH (US)

(73) Assignee: The Procter & Gamble Company, Cincinnati, OH (US)

( * ) Notice: Subject to any disclaimer, the term of this patent is extended or adjusted under 35 U.S.C. 154(b) by 219 days.

This patent is subject to a terminal disclaimer.

(21) Appl. No.: 13/026,548

(22) Filed: Feb. 14, 2011

(65) Prior Publication Data

US 2012/0208420 A1  Aug. 16, 2012

(51) Int. Cl.
*B32B 27/12* (2006.01)
*D04H 1/00* (2006.01)

(52) U.S. Cl.
USPC ............ 442/398; 442/327; 442/394; 442/399

(58) Field of Classification Search
USPC .................................. 442/327, 328, 394–399
See application file for complete search history.

(56) References Cited

U.S. PATENT DOCUMENTS

| | | |
|---|---|---|
| 3,860,003 A | 1/1975 | Buell |
| 4,808,178 A | 2/1989 | Aziz et al. |
| 4,909,803 A | 3/1990 | Aziz et al. |
| 5,151,092 A | 9/1992 | Buell et al. |
| 5,221,274 A | 6/1993 | Buell et al. |
| 5,554,145 A | 9/1996 | Roe et al. |
| 5,569,234 A | 10/1996 | Buell et al. |
| 5,580,411 A | 12/1996 | Nease et al. |
| 6,004,306 A | 12/1999 | Robles et al. |
| 6,120,487 A | 9/2000 | Ashton |
| 7,223,818 B2 | 5/2007 | Autran et al. |
| 7,491,770 B2 | 2/2009 | Autran et al. |
| 7,626,073 B2 | 12/2009 | Catalan |
| 2003/0022582 A1* | 1/2003 | Cree et al. ..................... 442/394 |
| 2004/0225044 A1 | 11/2004 | Chen |
| 2007/0249254 A1 | 10/2007 | Mansfield |
| 2009/0258210 A1 | 10/2009 | Iyad et al. |

OTHER PUBLICATIONS

U.S. Appl. No. 13/026,533, filed Feb. 14, 2011.
U.S. Appl. No. 13/026,563, filed Feb. 14, 2011
PCT International Search Report, mailed Apr. 17, 2012.(10 pages).

* cited by examiner

*Primary Examiner* — Jennifer A Steele
(74) *Attorney, Agent, or Firm* — Thibault Fayette; John G. Powell; Charles R. Ware

(57) ABSTRACT

A multilayer laminate material that resists the growth of a hole, tear, or aperture, and includes an extensible nonwoven layer joined to an elastomeric film layer in a face-to-face relationship. The elastomeric film layer includes an SEEPS elastomeric block copolymer that has a $T_m$ of between 10° C. and 20° C. The laminate exhibits a laminate integrity time of greater than 2 hours.

19 Claims, 4 Drawing Sheets

TEAR RESISTANT LAMINATE

FIELD OF THE INVENTION

The present invention is directed, generally, to a stretchable laminate that includes a film exhibiting improved resistance to the undesired growth of a tear, hole, aperture, or other discontinuity. Specifically, the present invention is directed to a laminate that includes an elastomeric film material formed from an elastomeric polymer that exhibits suitable strain crystallization properties, especially at the leading tip of a tear or other discontinuity in the film, to help resist undesired growth of the tear or discontinuity.

BACKGROUND OF THE INVENTION

Extensible laminate materials that include films, especially elastic films, are commonly used for a wide variety of applications. For example, disposable absorbent articles typically include one or more components that rely on the elastic properties provided by an elastomeric laminate to provide a comfortable, conforming fit when the article is worn by a wearer. While elastic films are known to provide desirable elastic behavior in certain absorbent article components (e.g., side panels, waist bands, leg bands), the films may not provide a desirable tactile sensation (e.g., softness or smoothness) on the skin of a wearer of the article. Thus, the elastic film is typically joined to another material, which is intended to remain in contact with the skin of the wearer and provide the desired tactile sensation. For example, it is not uncommon for an elastic film layer to be sandwiched between two plastically extensible nonwoven layers, which are selected to provide a desired feeling of softness.

In some instances, for example when an elastic laminate is desired, a laminate may be subjected to an incremental stretching process, sometimes referred to as activation. The incremental stretching process permanently, mechanically deforms the plastically extensible nonwoven material of the laminate, which reduces the tendency of the nonwoven to resist stretching. But the film layer still exhibits desirable elastic behavior. One drawback to conventional incremental stretching processes and other rigorous manufacturing processes (e.g., embossing, high pressure bonding, thermal bonding) is the undesirable formation of holes, tears, or other discontinuities in the elastic film layer of the laminate. Additionally, conventional elastic film material may form holes or tears when subjected to the normal wear and tear of an article during use (e.g., contact with sharp objects, pulling and stretching by a wearer, rigorous activity of a wearer, and/or repetitive mechanical stress experienced during wear). Initially, a tear may start out small and be relatively inconsequential with regard to the desired function of the film, laminate, article component, and/or article, but as the size of the tear grows (e.g., due to the mechanical rigors typically associated with the use of the laminate and/or during the manufacturing process), the likelihood of catastrophic failure of the film, laminate, article component, or article increases. Unintended catastrophic failure of an article or component is almost always undesirable, but when the article is a disposable absorbent article such as a diaper or training pant, the consequences of catastrophic failure of the article or component may be especially acute. For example, the contents of the diaper or pant may escape from the article and/or the article may even become separated from the wearer.

In certain applications, it may be desirable to provide a laminate comprising a film that has pre-formed discontinuities (e.g., one or more apertures that extend at least partially through the thickness of the film and/or laminate) in order to control, for example, the breathability, permeability to liquids and/or solids, opacity, extensibility, etc. of the laminate. But openings in the film and/or laminate, whether desired or undesired, may grow and ultimately lead to partial or complete failure of the film and/or laminate to function as intended. Further, at least some manufacturers desire thinner/lower basis weight films to reduce material costs related to incorporating such films into laminates and/or articles. The potential problems associated with the formation of tears, holes, and apertures in a film may be even more acute in thinner/lower basis weight films.

In order to reduce the possibility that the elastic film in an extensible laminate will fail due to the presence of a hole, tear, and/or aperture, it may be desirable to increase the strength of the film. However, increasing the strength of the film typically means increasing the thickness of the film or forming the film from different materials, both of which may undesirably impact the cost and/or complexity of manufacturing the laminate and/or the suitability of the laminate for a particular use. For example, using a stronger film in a laminate intended for use in a side panel of a disposable diaper may increase the pressure applied by the side panel to the skin of a wearer, potentially causing undesirable red-marking and/or discomfort to the wearer. Additionally, increasing the overall strength of the film may only improve the film and/or laminate's resistance to the initial formation of a hole or tear and not its subsequent growth.

Another method for reducing the possibility of undesired growth of a tear, hole, and/or aperture in a film, especially in a low basis weight film, includes joining one or more reinforcing layers to the film. For example, the film may be formed with one or more commonly known "skin layers" (e.g., through a co-extrusion process). However, adding skin layers to improve the performance of the film and/or laminate comprising the film may undesirably increase the cost and/or complexity of producing the laminate and/or make the laminate unsuitable for its intended purpose. Thus, there remains a need to provide an extensible laminate including an elastic film that exhibits resistance to the growth of tears, holes, and/or apertures in a variety of circumstances (e.g., at a low basis weight) without the use of additional reinforcing materials.

Accordingly, it would be desirable to provide an extensible laminate that includes an elastic film which exhibits improved resistance to the propagation of a tear, hole, or aperture.

SUMMARY OF THE INVENTION

In order to provide a solution to the problems set forth above, at least one embodiment herein discloses a multilayer laminate material that resists the growth of a hole, tear, or aperture. The laminate comprises at least one extensible nonwoven layer joined to at least one elastomeric film layer in a face-to-face relationship. The elastomeric film layer comprises an SEEPS elastomeric block copolymer that has a $T_m$ of between about 10° C. and 20° C. The laminate has a laminate integrity time of greater than about 2 hours according to the Laminate Integrity Test.

DETAILED DESCRIPTION OF THE INVENTION

Definitions

Figure 1:
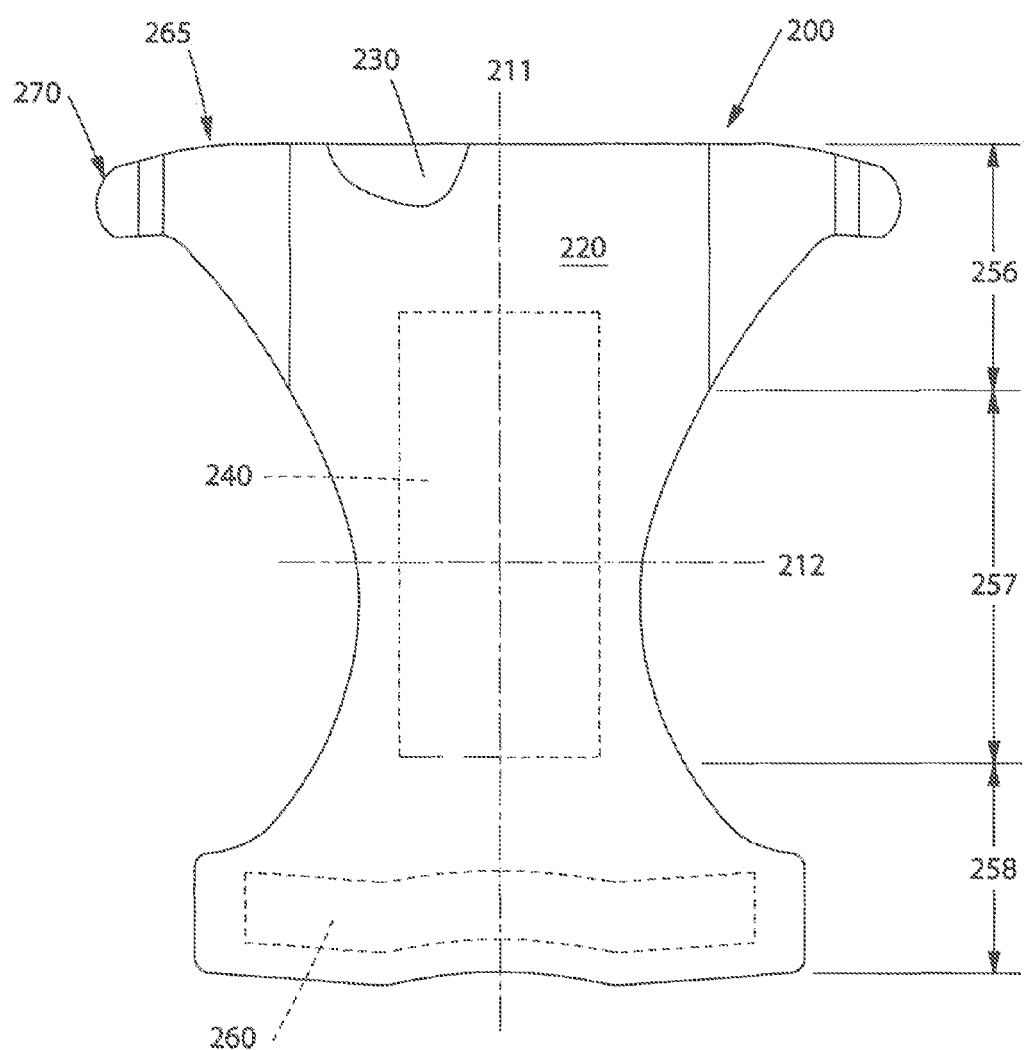
FIG. 1 is a plan view of an absorbent article.

"Absorbent article" means a device that absorbs and contains body exudates and, more specifically, devices that are placed against or in proximity to the body of the wearer to absorb and contain the various exudates discharged from the body. Exemplary absorbent articles include diapers, training pants, pull-on pant-type diapers (i.e., a diaper having a preformed waist opening and leg openings such as illustrated in U.S. Pat. No. 6,120,487), refastenable diapers or pant-type diapers, incontinence briefs and undergarments, diaper holders and liners, feminine hygiene garments such as panty liners, absorbent inserts, and the like.

"Activation" is the mechanical deformation of a plastically extensible material that results in permanent elongation of the extensible material in the direction of activation in the X-Y plane of the material. For example, activation occurs when a web or portion of a web is subjected to a stress that causes the material to strain beyond the onset of plasticity, which may or may not include complete mechanical failure of the material or portion of the material. Activation of a laminate that includes an elastic material joined to a plastically extensible material typically results in permanent deformation of the plastic material, while the elastic material returns substantially to its original dimension. "Activate," and variations thereof, means subjecting a material to an activation process.

"Aperture" means an opening in a film purposefully added during filmmaking or laminate making, which is intended to impart a desired characteristic such as breathability. The growth of an aperture is the increase in the size of the aperture due to mechanical failure of the portion(s) of the film adjacent to the aperture.

"Basis weight" is the mass of a sheet or web of material divided by its surface area. The units for basis weight herein are grams per square meter ($g/m^2$).

"Breathable" means a film or laminate that give Air Permeability Values of between 5 and 50 $m^3/m^2/min$ in the Air Permeability Test described below.

"Copolymer" means a polymer derived from two or more monomer species wherein the polymer chains each comprise repeat units from more than one monomer species.

"Crystalline melting temperatures" are determined by Differential Scanning calorimetry, which is described in more detail below. The melting endothermic peak temperature is taken as the $T_m$ ($T_{pm}$ per ASTM D3418-08) of a particular population of crystals. Materials of the current invention may have one or more melting endotherm peaks.

"Disposed" means an element is positioned in a particular place with regard to another element.

"Elastic," "elastomeric," and "elastically extensible" mean the ability of a material to stretch by at least 50% without rupture or breakage at a given load, and upon release of the load the elastic material or component exhibits at least 80% recovery (i.e., has less than 20% set). For example, an elastic material that has an initial length of 100 mm can stretch to at least 150 mm (50% stretch) and, upon removal of the force, retract to a length of 110 mm (i.e., have a set of 10 mm or 10%). Stretch, sometimes referred to as strain, percent strain, engineering strain, draw ratio, or elongation, along with recovery and set may each be determined according to the Hysteresis Test described in more detail below. It is to be understood; however, that this definition of elastic does not apply to materials that do not have the proper dimensions (e.g., not wide enough) to be properly subjected to the Hysteresis Test. Instead, such material is considered to be elastic if it can stretch to at least 50% upon application of a biasing force, and return substantially to its original length (i.e., exhibit less than 20% set) upon release of the biasing force.

"Extensible" means the ability to stretch or elongate, without rupture or breakage, by at least 50%.

"Film" means a sheet-like material wherein the length and width of the material far exceed the thickness of the material (e.g., 10×, 50×, or even 1000× or more). Films are typically liquid impermeable but may be configured to be breathable.

"Hole" means an undesired opening in a film that can act as a "crack" in the Fracture Mechanics sense. The growth of a hole is the increase in the size of the hole due to mechanical failure of the portion(s) of the film adjacent to the hole.

"Joined" means configurations whereby an element is directly secured to another element by affixing the element directly to the other element, and configurations whereby an element is indirectly secured to another element by affixing the element to intermediate member(s) that in turn are affixed to the other element.

"Laminate" means two or more materials that are bonded to one another by any suitable method known in the art (e.g., adhesive bonding, thermal bonding, ultrasonic bonding, or high pressure bonding using non-heated or heated patterned roll).

"Longitudinal" means a direction running substantially perpendicular from a waist end edge to an opposing waist end edge of an absorbent article when the article is in a flat out, uncontracted state, or from a waist end edge to the bottom of the crotch in a bifolded article. Directions within 45 degrees of the longitudinal direction are considered to be "longitudinal." "Lateral" refers to a direction running from a side edge to an opposing side edge of an article and generally perpendicular to the longitudinal direction. Directions within 45 degrees of the lateral direction are considered lateral.

"Machine direction" or "MD" is the direction parallel to the direction of travel of the web in a manufacturing process. The "cross machine direction" or "CD" is the direction substantially perpendicular to the MD and in the plane generally defined by the web.

"Nonwoven" means a porous, fibrous material made from continuous (long) filaments (fibers) and/or discontinuous (short) filaments (fibers) interlaid in an irregular fashion by processes such as, for example, spunbonding, meltblowing, air laying, coforming, carding, hydroentangling, and the like. The fibers of the nonwoven material may be bonded together using conventional techniques, such as thermal point bonding, ultrasonic point bonding, adhesive pattern bonding, and adhesive spray bonding. Nonwovens do not have a woven or knitted filament pattern. Nonwovens may be liquid permeable or impermeable.

"Plastic" and "plastically extensible" mean the ability of a material to stretch by at least 50% without rupture or breakage at a given load and, upon release of the load the material or component, exhibits at least 20% set (i.e., recovers less than 80%). For example, an extensible material that has an initial length of 100 mm can stretch at least to 150 mm (50% stretch) and, upon removal of the applied force, retract to a length of 135 mm (i.e., have a set of 35 mm (35% set), when subjected to the Hysteresis Test described below.

"Relaxed" means the state of an element, material or component at rest with substantially no external force acting on the element, other than gravity.

"Tear" means an undesired opening in a film that has intersected with one or more of the edges of the film, which can act as a "crack" in the Fracture Mechanics sense. The growth of a tear is the increase in the size of the tear due to mechanical failure of the portion(s) of the film adjacent to the tear.

"Web" means a material capable of being wound into a roll. Webs may be films, nonwovens, laminates, apertured films and/or laminates, and the like. The face of a web refers to one of its two dimensional surfaces, as opposed to its edge.

"X-Y plane" means the plane defined by the MD and CD of a moving web or the length and width of a piece of material.

Polymer

A number of elastomeric polymers can be used to make an elastic film. Nonlimiting examples of elastomeric polymers include homopolymers, block copolymers, random copolymers, alternating copolymers, graft copolymers, and the like. Particularly suitable polymers for use in films exhibiting resistance to tear propagation are block copolymers, which are typically made of blocks (or segments) of distinct repeat units that each contribute to the properties of the polymer. One reason block copolymers are recognized as being useful, at least in part, is because the blocks of the copolymer are covalently bonded to one another and form microphase-separated structures with rubber domains that provide good extensibility while the glassy end block domains provide mechanical integrity (e.g., good mechanical strength and avoidance of unwanted stress relaxation or flow). Block copolymers suitable for use herein may exhibit both elastomeric and thermoplastic characteristics. For example, the end-blocks may form domains that display stiff, rigid mechanical properties at temperatures that prevail during end use (e.g., 20° C.-40° C.), thereby adding rigidity and strength to the entire polymer. Such an end-block is sometimes referred to as a "hard block". The midblock may accommodate the relatively large deformations associated with elastomers and provides retractive force when the material is strained (i.e., stretched or extended). Such a midblock is sometimes referred to as a "soft block" or "rubbery block." Suitable block copolymers for use herein include at least one hard block (A) and at least one soft block (B). The block copolymers may have multiple blocks. In certain embodiments, the block copolymer may be an A-B-A triblock copolymer, an A-B-A-B tetrablock copolymer, or an A-B-A-B-A pentablock copolymer. Other suitable copolymers include triblock copolymers having endblocks A and A', wherein A and A' are derived from different compounds. In certain embodiments, the block copolymers may having more than one hard block and/or more than one soft block, wherein each hard block may be derived from the same or different monomers and each soft block may be derived from the same or different monomers.

Suitable hard block components have a glass transition temperature ($T_g$) greater than 25° C. or 45° C. or even 65° C., but typically less than 100° C. The hard block portion may be derived from vinyl monomers including vinyl arenes such as styrene and alpha-methyl-styrene or combinations thereof. The soft block portion may be a polymer derived from conjugated aliphatic diene monomers. Typically, the soft block monomers contain fewer than 6 carbon atoms. Suitable diene monomers such as, for example, butadiene and isoprene may be used as-polymerized or in their hydrogenated form. Suitable soft block polymers include poly(butadiene), poly(isoprene), and copolymers of ethylene/propylene, ethylene/butene, and the like. In certain embodiments, it may be desirable to partially or fully hydrogenate any residual olefinic double bonds contained in the copolymer or portion thereof (e.g., midblock or endblock).

In a particularly suitable embodiment, the elastomeric polymer may be a styrene-ethylene-ethylene-propylene-styrene ("SEEPS") block copolymer that includes two polystyrene endblocks of approximately 8 kg/mole each and a 45 kg/mole midblock. The midblock may be formed, for example, by copolymerizing and then hydrogenating isoprene and butadiene. It may be desirable to hydrogenate the copolymer such that from 95-99% or even 98-99% of the original C=C double bonds in the midblock are saturated but the polystyrene endblocks remain aromatically intact. If the degree of hydrogenation is too low, the polymer may begin to lose its ability to undergo strain-induced crystallization. It is believed, without being limited by theory, that strain induced crystallization in a polymer is important for providing tear resistant characteristics to films made with such polymers. In certain embodiments, copolymerizing isoprene and butadiene to produce the rubbery midblock may result in a copolymer that varies both in comonomer sequence and in vinyl content. While a SEEPS copolymer is a block copolymer, the ethylene-ethylene-propylene ("EEP") midblock is more of a random copolymer than blocky or alternating. But subtle departures from randomness may occur. The departures from randomness, as well as the vinyl content of the copolymer, may be controlled by adjusting the conditions during polymerization. For example, copolymerization of isoprene and butadiene with subsequent hydrogenation may give rise to a variety of branch types. Table 1 below exemplifies the different branch types that may result. With the partial exception of the methyl branches, the branches typically do not "fit" into the polyethylene-type crystals, and therefore decrease the midblock's degree of crystallinity and $T_m$. For example, the midblock of a SEEPS block copolymer may be approximately 7% crystalline at temperatures below −50° C. and have a $T_m$ of approximately 0° C. In comparison, a substantially unbranched polyethylene is approximately 75% crystalline and has a $T_m$ of approximately 135° C.

TABLE 1

| Isomer | Branch Type After Hydrogenation |
|---|---|
| 1,2 Isoprene | Methyl, Ethyl |
| 3,4 Isoprene | Isopropyl |
| 1,4 Isoprene | Methyl |
| 1,2 Butadiene | Ethyl |
| 1,4 Butadiene | No branch - possible to crystallize |

The length of the runs of crysallizable $CH_2$ sequences, which directly impact the melting temperature of the polymer midblock, depends, at least partially, on the sequence of comonomer incorporation into the midblock (e.g., isoprene always gives a branch of some type) and the overall balance between 1,4 and 1,2 (or 3,4) polymerization of the dienes. The $T_m$ of the crystal may provide information about the length of the crystallizable sequences and the ability of the material to undergo strain-induced crystallization, both of which are related to the number, type, and distribution of the branches on the midblock backbone. Suitable elastomers herein include sufficiently long crystallizable sequences of $CH_2$ groups (which form polyethylene-type crystals) that have a $T_m$ of greater than 10° C. (compared to, e.g., −5° C. for previously known materials). A suitable $T_m$ for the elastomers herein is between 10° C. and 20° C.; 12° C. and 18° C.; 13° C. and 17° C.; or even between 14° C. and 16° C.

In addition to the EEP midblocks described above, it may be desirable to provide a midblock of the "EB" type (i.e., hydrogenated polybutadiene) that contains similar crystallizable sequences, for example, by choosing the appropriate solvent polarity (which controls 1-4 vs. 1-2 content), as described in *Anionic Polymerization: Principles and Practical Applications*, Henry Hsieh, Roderick Quirk; Chapter 9, pp. 197-229; Marcel Decker, New York (1996).

Film

The extensible laminates disclosed herein include an elastomeric, tear-resistant film layer. Unlike conventional elastomeric films (e.g., films formed from known elastomers such as Vector 4211 from Dexco Polymers L.P., Houston, Tex.), which form films that exhibit minimal or no tear resistance, the elastic films herein include an effective amount of at least one elastic polymer that imparts suitable tear resistance to the film. It is to be appreciated that such resistance is not limited to tears, but also includes slits, apertures, openings, holes, and/or any other discontinuities in the film. The Slow Tear Test set forth in co-pending U.S. Ser. No. 13/026,533, titled "Tear Resistant Film," filed by Mansfield on Feb. 14, 2011, provides a suitable method for quantifying a film's resistance to the growth of a tear, hole, aperture, or other discontinuity. Suitable time-to-fail values include values of greater than 1 hour, 2 hours, 4 hours, 6 hours, 10 hours, 15 hours, or even up to 24 hours or more, for example up to 30 hours, 36 hours, 40 hours, 44 hours, 48 hours, or even up to 60 hours when measured according to the Slow Tear Test. Ideally, the film is capable of resisting the growth of a tear indefinitely. While the present films desirably provide suitable resistance to the growth of a tear as described herein, it may also be desirable for the films herein to exhibit resistance to the rapid application of a relatively high amount of mechanical stress. For example, the present films may have a High-Speed Tensile Strength of between 10 and 25 MPa; 15 and 20 MPa; 16 and 19 MPa; or even between 17 and 18 MPa when measured according to the High Speed Tensile Test set forth in the aforementioned copending application titled "Tear Resistant Film." It may further be desirable to provide a film that exhibits a Notched High Speed Tensile Strength of between 10 and about 20; MPa; 14 and 19 MPa; or even between 15 and 18 MPa when measured according to the Notched High-Speed Tensile Strength Test set forth in the aforementioned copending application titled "Tear Resistant Film." It is believed, without being limited by theory, that suitable High Speed Tensile and/or Notched Tensile Strengths in a film may be important for providing at least some resistance to film failure related to relatively high rates of undesired mechanical stress.

The present tear resistant films are not limited to any particular dimension, and may be configured as relatively thin sheets of material. In certain embodiments, the film may have an Effective Average Thickness of between 1 μm-1 mm; 3 μm-1 500 μm; or 5 μm-100 μm, or any value in these ranges. Suitable basis weight ranges for the films disclosed herein include from 20 to 140 g/m$^2$, for example from 25 to 100 g/m$^2$; from 30 to 70 g/m$^2$; or even from 35 to 45 g/m$^2$, according to the Basis Weight Test below. The tear resistant films may be formed by any suitable method in the art such as, for example, extruding a molten thermoplastic and/or elastomeric polymer through a slit die and subsequently cooling the extruded sheet. Other non-limiting examples for making films include casting, blowing, solution casting, calendering, and formation from aqueous or cast, non-aqueous dispersions. Suitable methods of producing films from polymeric materials are described in *Plastics Engineering Handbook of the Society of the Plastics Industry, Inc.*, Fourth Edition, 1976, pages 156, 174, 180 and 183. In certain embodiments, the elastic film may have a loading engineering stress at 200% strain (L200) of between about 0.8 and 2 MPa, 1.0 and 1.5 MPa, or even between 1.0 and 1.2 MPa, and an unloading engineering stress at 50% strain (UL50) of between 0.3 and 0.8, 0.4 and 0.6, or even between 0.5 and 0.6 MPa according to the Hysteresis Test described in more detail below. The L200 and UL50 values disclosed above may be important for providing a film that is suitable for use in a laminate and/or disposable absorbent article (e.g., for providing low force recovery stretch, a snug comfortable fit, less undesired sag, containment of bodily exudates in a desired location, strength to resist the initial formation of a hole or tear).

Other exemplary films suitable for use in the present tear resistant laminates are disclosed in the aforementioned copending application titled "Tear Resistant Film."

Laminate

The present tear resistant laminates are not limited to any particular configuration and may include an elastic film layer joined to one or more nonwoven and/or film layers, as desired, as long as the laminate exhibits suitable tear resistance. For example, a tear resistant laminate should have a minimum laminate integrity time, when tested according to the Laminate Integrity Test described hereinbelow, of greater than 2 hours, 5 hours, 10 hours, 20 hours, 30 hours or even greater than 50 hours, but typically less than 100 hours. Ideally, the tear resistance laminates described herein can resist the growth of a hole, tear, or aperture indefinitely. In certain embodiments, the laminate may include a tear resistant, elastomeric film layer having a basis weight of between 50 and 100 grams per square meter ("gsm") sandwiched between two nonwoven layers each having a basis weight of between 8 and 100 gsm. The film and nonwoven layers of the extensible laminate may be joined together by any suitable means known in the art (e.g., adhesives, cohesives, thermal bonding, combinations of these, and the like). In certain embodiments, the nonwoven layers may each be formed as laminates of two more layers, for example, in a commonly known spunbond-meltblown-spunbond (SMS) configuration. Each nonwoven layer in the exemplary SMS configuration may have a basis weight of between 1 and 25 gsm, 2 and 20 gsm, or even between 3 and 10 gsm. A particularly suitable example of an SMS nonwoven includes spunbond layers having a basis weight of between 5 and 25 gsm and a meltblown layer having a basis weight of between 1 and 5 gsm.

The fibers may be formed from any suitable plastic material, elastic material, or combination thereof commonly known in the art for making nonwoven fibers, and may be formed as monocomponent fibers, bicomponent fibers, multicomponent fibers, or combinations of these. Suitable examples of elastomeric materials include styrenic block copolymers, elastomeric polyolefins, and polyurethanes. Particularly suitable examples of elastic materials for making fibers include an elastomeric polypropylene resin available from ExxonMobil, Houston, Tex. under the tradename VISTAMAXX. Suitable polymers for forming plastically extensible fibers are not particularly limited as long as they have plastic deformation properties. Nonlimiting examples of suitable plastic polymers include polyolefins generally, polyethylene, linear low density polyethylene, polypropylene, ethylene vinyl acetate, ethylene ethyl acrylate, ethylene acrylic acid, ethylene methyl acrylate, ethylene butyl acrylate, polyurethane, poly(ether-ester) block copolymers, poly(amide-ether) block copolymers, and combinations thereof. The fibers may be configured as monocomponent, bicomponent, or multicomponent fibers. For example, the fibers may be core-sheath type bicomponent fibers configured to have a polypropylene core and polyethylene sheath.

In certain embodiments, the nonwoven material may be configured to include two or, optionally, three layers of fibers. In such an embodiment, the first layer of fibers may be spunbond fibers having a first number-average fiber diameter of between 10 µm to 30 µm, for example, 15 µm to 25 µm. The second layer of fibers may be meltblown fibers having a second number-average fiber diameter that is smaller than the first number-average fiber diameter (e.g., from 1 µm to 10 µm, for example 1 µm to 5 µm). The third layer of fibers, when provided, may be nanofibers having a third number-average fiber diameter that is smaller than the second number-average fiber diameter (e.g., between 0.1 µm to 1 µm, for example 0.5 µm). The ratio of the first diameter to the second diameter may be from 2 to 50, or 3 to 10, for example 5. The ratio of the second diameter to the third diameter may be 2 to 10 or, for example, 5. In certain embodiments, the second layer of fibers may be disposed on the first layer of nonwoven fibers, and the third layer of fibers (when included) may be disposed on the second layer of fibers. This arrangement may include embodiments where the first and second (and optionally third) fiber layers form essentially adjacent layers such that a portion of the layers overlap to form an interpenetrating fiber network at the interface (e.g., fibers from the first and second layers overlap and/or fibers from the second and third layers overlap). This arrangement may also include embodiments where the first and second fiber layers are essentially completely intermingled to form a single heterogeneous layer of interpenetrating fibers. In certain embodiments, the laminate may be configured as a two layer laminate with a first layer of spunbond fibers joined to a second layer of meltblown micro- and/or nano-fibers, which are selected to provide a suitable bond (e.g. adhesive bond) between the spunbond fiber layer and the tear resistant film layer in the laminate. In certain embodiments, the nonwoven may include at least four, and optionally five, layers of fibers of differing kinds in a stacked arrangement. For example, the nonwoven may be arranged in an SMNS, SMNM or SMNMS configuration (i.e., spunbond, meltblown, nanofiber, meltblown, and spunbond).

The fine fibers of the meltblown layer may enhance the opacity of the laminate, which is typically a desirable feature. The meltblown fibers may also have the beneficial effect of improving the structural integrity of the nonwoven material when the meltblown fibers overlap and are dispersed among the other nonwoven fibers of the nonwoven material, for example in an SMS nonwoven laminate in which the meltblown layer is disposed between and joined to two spunbond layers. The self-entanglement resulting from the incorporation of fibers having substantially different length scales can increase the internal adhesive integrity of the nonwoven material, thereby lessening (and potentially even eliminating) the need for the bonding of the nonwoven material. The meltblown fibers can also form a "tie-layer" increasing the adhesion between the other nonwoven fibers and an adjacent polymeric layer, in particular when the meltblown fibers are formed from an adhesive material.

The first (top) layer may include spunbond fibers. The second layer may be disposed on the first layer and can include meltblown fibers. The third layer may be disposed on the second layer and can include nanofibers. The fourth layer may be disposed on the third layer and can include meltblown fibers. The optional fifth (bottom) layer may be joined to the fourth layer and may include spunbond (or, alternatively, carded) fibers that are generally either plastic fibers (for example including high-extensibility nonwoven fibers or a high-elongation carded web material) or plastoelastic blend fibers. When the fifth layer includes plastic fibers, it may be advantageous to provide plastic fibers that are extensible enough to survive the mechanical activation process. Suitable examples of such sufficiently deformable spunbond fibers are disclosed in WO 2005/073308 and WO 2005/073309. Suitable commercial plastic fibers for the fifth layer include a deep-activation polypropylene, a high-extensibility polyethylene, and polyethylene/poly-propylene bi-component fibers (all available from BBA Fiberweb Inc., Simpsonville, S.C.). The fifth layer can be added to the nonwoven material at the same time as the first four layers, or the fifth layer can be added later in a production process for an absorbent article. Adding the fifth layer later in the production process permits greater SOC flexibility, for example allowing the intercalation of absorbent article components (e.g., a high-performance elastomeric band) into the SOC and permitting the omission of the fifth layer in regions where it is not required in the absorbent article (e.g., where the SOC is positioned on the absorbent core).

Other exemplary stretch laminate configurations and methods of making stretch laminates suitable for use herein are disclosed in U.S. Publication No. 2007/0249254, filed by Mansfield on Apr. 24, 2006 and titled "Stretch Laminate, Method of Making and Absorbent Article."

Article

In certain embodiments, the present tear resistant laminates may be incorporated into an article (e.g., a diaper or training pant), where it is particularly important that the article function as intended for a particular amount of time. Thus, suitable laminate integrity times and time-to-fail values are important for providing an indication that an article or article component that includes the laminate or film is less likely to suffer catastrophic failure in use.

FIG. 1 shows an exemplary embodiment of a diaper 200 in a flat-out, uncontracted state (i.e., with no elastic induced contraction). Portions of FIG. 1 are cut away to more clearly show the construction of the diaper 200. The outer, garment-facing surface of the diaper 200 is oriented towards the viewer and the opposing inner, wearer-facing surface is oriented away from the viewer. The diaper 200 as shown in FIG. 1 has a longitudinal centerline 211 extending in the longitudinal direction and a lateral centerline 212 orthogonal thereto. The diaper 200 may include a first waist region 256, a second waist region 258, and a crotch region 257 disposed therebetween. As shown in FIG. 1, the diaper 200 may include a liquid pervious topsheet 230; a liquid impervious outer cover 220 joined with at least a portion of the topsheet 230, for example, along the periphery of the diaper 200; and an absorbent core assembly 240 positioned between the topsheet 230 and the outer cover 220. The inner, wearer-facing surface of the diaper 200 may include at least a portion of the topsheet 30 and other components, which may be joined to the topsheet 30. The outer, garment-facing surface may include at least a portion of the outer cover 220 and other components, which may be joined to the outer cover 220. The diaper 200 may include an elastic waist feature 260 and a fastening system. The fastening system may include an ear 265 joined to at least one of the front and back waist regions 256 and 258 and extending laterally outward therefrom. In certain embodiments, the ear 265 and one or both waist regions 256 and/or 258 may be formed from as a unitary structure, for example, by forming the two elements from the same substrate. The ear 265 may include a fastening tab 270, which extends laterally outwardly therefrom. The fastening tab 270 may include a fastening element that is engageable with another portion of the diaper 200. "Engageable" means one element is configured to be joined to another element, for example, through the creation of an entanglement-type mechanical bond. Nonlimiting examples of suitable absorbent articles for use with the tear resistant film disclosed herein may be found in U.S. Pat. Nos. 3,860,003; 4,808,178; 4,909,803; 5,151,092; 5,221,274; 5,554,145; 5,569,234; 5,580,411; 6,004,306; 7,626,073; U.S. Publication No. 2007/0249254; and copending U.S. Ser. No. 13/026,563, titled "Absorbent Article With Tear Resistant Components" filed on Feb. 14, 2011 by Mansfield.

Test Methods.

Environmental conditions for the test methods herein include a temperature of 23° C.±2° C., unless indicated otherwise. In some instances, a film sample to be tested may include one or more layers of other material joined to the film material (e.g., samples taken from commercially available articles). In such instances, the film is carefully separated from the other layers of material so that damage to the film is avoided. If the film is damaged (i.e., torn, cut, punctured, etc.) as a result of separating the film from the other material, discard the sample and obtain another that is undamaged.

Hysteresis

Figure 2:
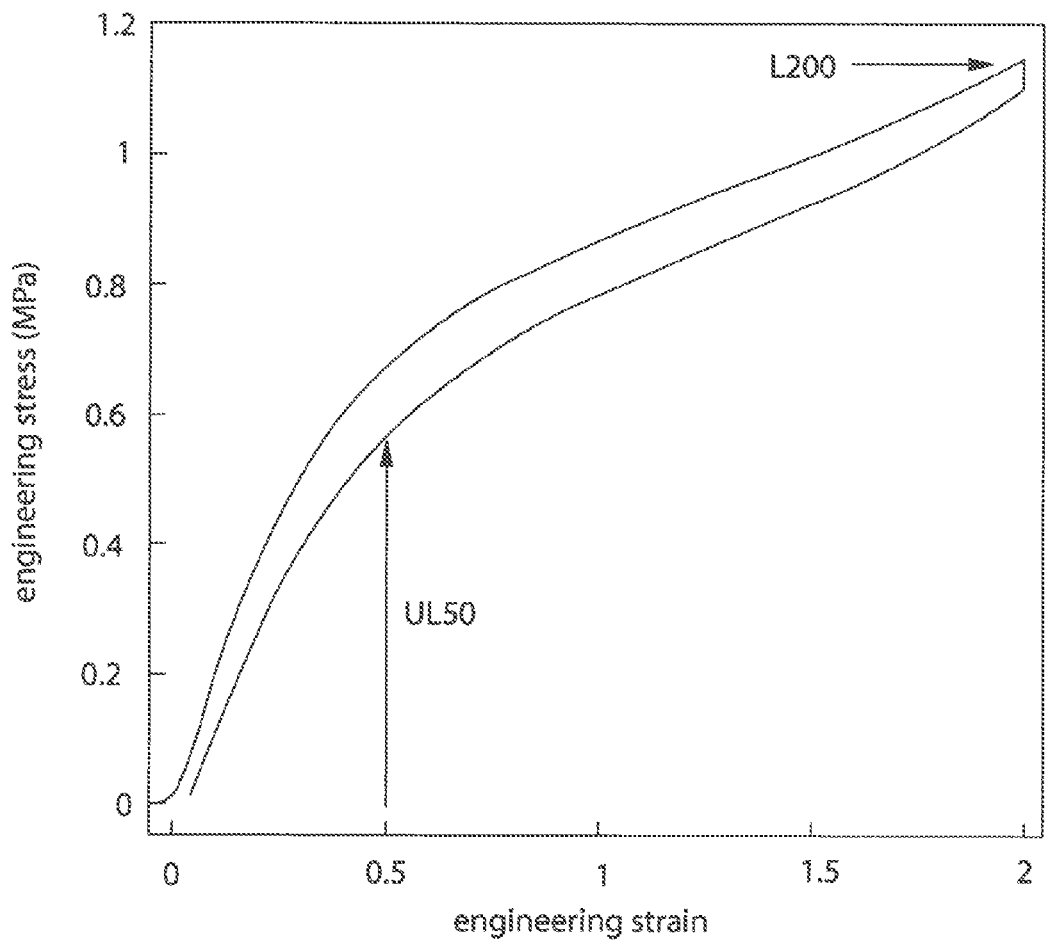
FIG. 2 is a chart illustrating an exemplary stress-strain curve generated during the Hysteresis Test.

The Hysteresis Test is performed in accordance with ASTM D882-02 using line-contact grips and a load-hold-unload sequence, along with the exceptions and/or conditions set forth below. FIG. 2 is provided to illustrate the portion of the stress-strain curve that includes the L200 value (i.e., the engineering stress at 200% strain during loading) and the UL50 value (i.e., the engineering stress at 50% strain during unloading) generated during the Hysteresis Test. One load-unload cycle is a run.

specimen width: 25.4 mm
gauge length: 25.4 mm
testing speed: 4.233 mm/s
temperature: 22-24 C
applied displacement: 50.8 mm (200% engineering strain)
hold time at the applied displacement: 30 seconds
If grip design does not accommodate the 50 mm extra sample length indicated in section 6.1 of ASTM D882-02, prepare samples to a length that allows gripping the appropriate gauge length without interfering with other parts of the grip. In such cases care must be taken to mount the specimen with proper alignment, gripping and gauge definition.

Record the following:
engineering stress at 200% engineering strain during the load segment (L200)
engineering stress at 50% engineering strain during the load segment (UL50)
engineering strain during unloading where the sample goes slack (Ls).

The set is then defined as Ls, expressed as a proportion of the engineering strain at applied displacement. For example if 200% engineering strain is applied to the sample and it goes slack at an engineering strain of 20% during unloading, the set is calculated as 20%/200%=0.10=10%.

When using the hysteresis test to determine whether a material meets the definition of "elastic" or "plastic" as described in the definitions, an applied displacement of 12.7 mm (i.e. an engineering strain of 50%) is used.

Basis Weight (Mass Per Unit Area)

The basis weight of a film sample is determined according to INDA Standard Test WSP 130.1 (09). All conditioning and testing is conducted in an atmosphere of 23±2° C., and 50±5% relative humidity.

The average of 5 specimens is reported as the Average Basis Weight in grams per square meter to 3 significant digits.

Effective Average Thickness

The Effective Average Thickness of the film is calculated from the Average Basis Weight as follows.

Effective Average Thickness=Average Basis Weight/density

Units:
Thickness: micrometers (μm)
Basis Weight: gsm
density=0.92 grams per cm³ (g/cc)
Results are reported in microns (μm) to 3 significant digits.

Air Permeability Test

The air permeability of a substrate (e.g., film, laminate, or article component) is determined by measuring the flow rate of standard conditioned air through a test specimen driven by a specified pressure drop. This test is particularly suited to materials having relatively high permeability to gases, such as nonwovens, apertured films and the like. ASTM D737 is used, except for the following modifications.

A TexTest FX3300 instrument or equivalent is used, which are available from Textest AG, Switzerland, or from Advanced Testing Instruments ATI in Spartanburg, S.C. The procedures described in the Operating Instructions for the TEXTEST FX 3300 Air Permeability Tester manual for the Air Tightness Test and the Function and Calibration Check are followed. If a different instrument is used, similar provisions for air tightness and calibration are made according to the manufacturer's instructions.

The test pressure drop is set to 125 Pascal and the 5 cm² area test head (model FX3300-5) is used. After making the measurement of a specimen according to the procedure given in the Operating Instructions for the TEXTEST FX 3300 Air Permeability Tester manual, the result is recorded to three significant digits. Five specimens are measured and the average of the five air permeability values is calculated and reported as the Air Permeability Value in m³/m²/min.

Differential Scanning Calorimetry (DSC)

Figure 3:
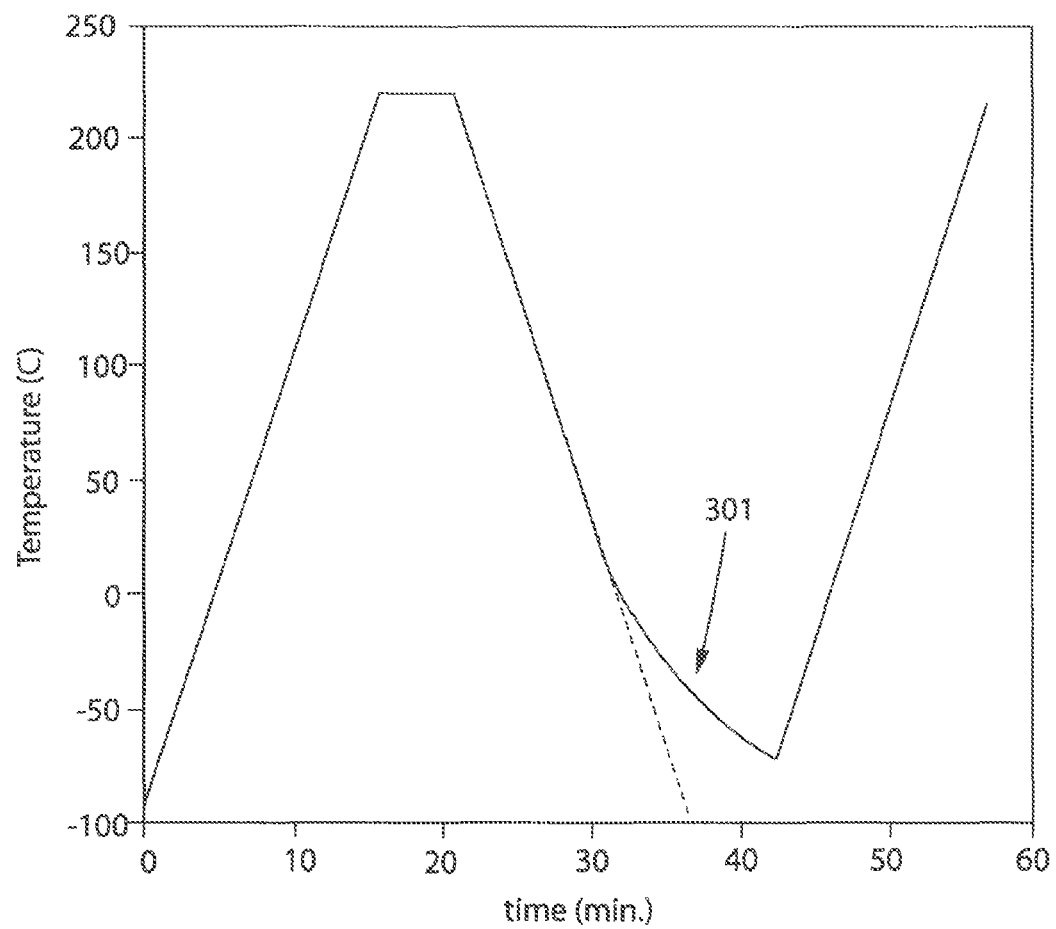
FIG. 3 is a chart of time versus temperature for use with the DSC test.

The DSC test is used to measure the $T_m$ of a polymer. The $T_m$ is determined by DSC measurements according to ASTM D3418-08 (note that $T_m$ is referred to as $T_{pm}$ in the ASTM method), except that the time-temperature profile shown in FIG. 3 is used for the measurement. Calibration is performed with a heating rate of 20° C./min. The temperature profile may include the non-linear portion 301 of profile at Time=30-42 minutes, as shown in FIG. 3. The non-linear portion 301 is a manifestation of limitations in the cooling capability of the apparatus. It is recognized that this deviation from the nominal cooling rate might have a modest effect on the observed melting curve, but all DSC data herein follow the same profile.

Laminate Integrity Test

Figure 4A:
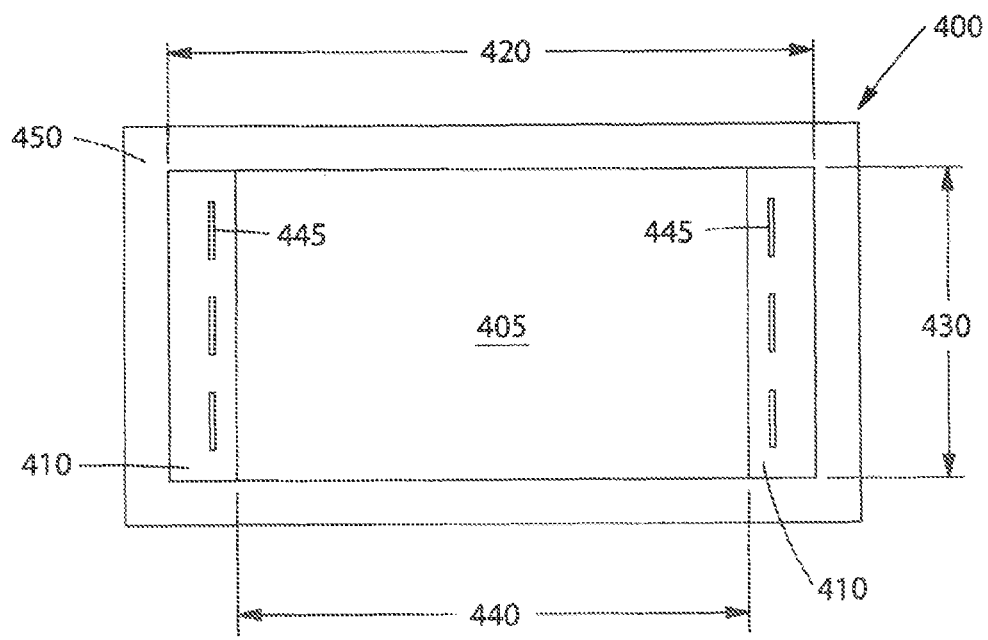
FIG. 4A is a top plan view of an exemplary laminate sample prepared according to the Laminate Integrity Test.
Figure 4B:
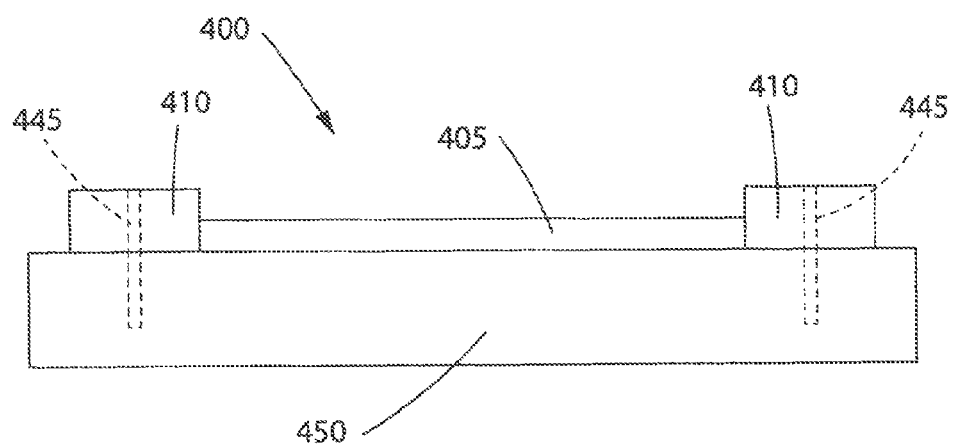
FIG. 4B is a side view of the sample in FIG. 4A.

This test provides an assessment of the mechanical integrity of a stretch laminate by applying an engineering strain of 100% to the stretch laminate along its stretch direction and monitoring said laminate for initiation and growth of holes or tears while holding it at a temperature of 37.8° C. FIGS. 4A and 4B are provided to illustrate certain aspects of the Laminate Integrity Test. FIG. 4A shows a top, plan view of the sample 400, and FIG. 4B shows a side view of the sample 400.

Prepare a sample 400 by cutting a rectangular piece of laminate 405 having the following dimensions:
Length 420: 100 mm (along direction of laminate stretch)
Width 430: 50.8 mm (perpendicular to direction of laminate stretch)
Gauge length 440: 80 mm (along direction of laminate stretch)

Take care to avoid nicking or otherwise damaging the edges of the sample 400, as described in ASTM D882-02. Sandwich the ends of the sample 400 between layers of masking tape 410 such that the inboard edges of the tape 410 define a gauge length 440 of 80 mm on the sample 400. One end of the sample 400 is stapled to a rigid piece of cardboard 450 sufficiently large in size to hold the sample 400 in a stretched configuration for the duration of the test. The staples 445 fasten the sample 400 to the cardboard 450 as shown in the diagram and are suitably spaced and positioned along substantially the entire width of the specimen. The staples 445 are located in the masking tape 410 within a millimeter of the edge that defines the gauge length 440 of the sample. The other end of the sample 400 (i.e., the non-stapled end) is displaced 80 millimeters so that the sample is deformed to an engineering strain of 100%. Staples 445 are then applied to fasten the other end of the sample 400 to the cardboard 450 as shown in the diagram. The cardboard 450 with the sample stapled thereto is then placed in a chamber or room maintained at a temperature of 37.8° C. The samples are monitored for initiation and growth of holes or tears, either visually or with use of video cameras. The size of the hole/crack/tear (expressed as a fraction of the sample's overall width) is recorded as a function of time. An adequate number of data points are acquired to enable a reasonable estimate of the time when the tear progresses to 50% of the sample's width. This time is the laminate integrity time.

If available material is not sufficiently large to prep samples with these dimensions, smaller samples may be used provided the displacement imposed on the specimen is decreased proportionally to achieve an engineering strain of 100%.

Examples

Table 2 shows the formulas for making various film Samples. The S4033, JL-007, and JL-014 shown in Table 2 are hydrogenated SEEPS block copolymers available from Kuraray America, Inc. in Pasadena, Tex. S4033 is a known SEEPS block copolymer, while the JL series (e.g., JL-007 and JL-014) may be thought of as S4033-type block copolymers modified for improved processability. The JL-series of SEEPS block copolymers have a mass ratio of isoprene to 1,3 butadiene of from 46/54 to 44/56 (e.g., 45/55). The oil in Table 2 is a white mineral oil such as Drakeol 600, Hydrobrite 550, or Krystol 550. REGALREZ 1126 and REGALITE 1125 are tackifiers available from Eastman Chemical Company in Kingsport, Tenn. The PS 3190 is a polystyrene homopolymer available from NOVA Chemical Company, Canada. AO is a suitable antioxidant such as Irganox 100 available from Ciba Specialty Chemicals in Switzerland.

Samples 1-11 are produced by extruding a thermoplastic composition through a slot die to form a film that is 100 mm wide and 100 µm thick. The thermoplastic composition is formed by extruding material in a Leistritz (27 mm) twin screw extruder with extended mixing sections. First, the oil and Septon polymers are mixed together, and then the polystyrene and tackifier are blended into the mixture, which is then fed into the extruder. Temperatures in the extruder typically range from 170-230° C. Subsequently, the compositions are formed into films using a ThermoFisher 20 mm single screw extruder. Temperatures in the ThermoFisher extruder typically range from 170-230° C.

Table 3 illustrates the time-to-fail and melt temperatures of various elastomeric film materials. Samples 1-6 and 9-10 are provided to show suitable examples of the present film. Samples 7 and 11 are provided as comparative examples to show that not all SEEPS block copolymers necessarily provide suitable tear resistance and/or processability. The time-to-fail measurements are obtained according to the Slow Tear Test and the $T_m$ values are obtained according to the DSC method. Samples 12-15 in Table 3 are formed by a two-stage compression molding procedure where the elastomer is compressed between heated platens (215° C.) and held for a dwell time of 3 minutes using shims that give a thick sheet of elastomer (approximately 2.5 mm thick) then subsequently folding and stacking the thick film and pressing without a shim and holding for a dwell time of about 30 seconds to give a film of between 80-200 µm in thickness. The percentages of the various ingredients are all weight percentages based on the weight of the film. Sample 12 is provided as a comparative example and is formed from 56% S4033, 13% PS3160, and 31% white mineral oil. Samples 13-15 include the same relative amounts of SEEPS block copolymer, polystyrene homopolymer, and mineral oil as Sample 12, but vary in the kind of SEEPS copolymer, including the $T_m$ of the polymer, used in their formation. Sample 13 is formed using 56% JL-007. Sample 14 is formed using JL-014. Sample 15 is formed using JL-013. These ingredients are added to a small batch mixer (Haake) and mixed at 50 RPM at a temperature of 210° C. for 3 minutes. Sheets are subsequently produced by pressing between heated platens held at 210° C.

TABLE 3

| Sample No. | time-to-fail (hr.) | $T_m$ (° C.) |
|---|---|---|
| 1 | 7.2 | 17.7 |
| 2 | 8.3 | 16.1 |
| 3 | 31.5 | 15.1 |
| 4 | 17.5 | 16.2 |
| 5 | 13.7 | 14.5 |
| 6 | 11.6 | 16.6 |
| 7 | 1.6 | 2.4 |
| 8 | 9.6 | 13.9 |
| 9 | 10.2 | 15.7 |
| 10 | 0.9 | 14.6 |
| 11 | 0.3 | 1.8 |
| 12 | 0.5 | −1.0 |
| 13 | 2.1 | 13.0 |
| 14 | 0.8 | 13.0 |
| 15 | 7.0 | 18.0 |

As can be seen Table 3, the Samples that include the S4033 SEEPS block copolymer fail to provide a time-to-fail of about an hour or more and/or a $T_m$ of between 10 to 20° C., whereas

TABLE 2

| | Sample # | | | | | | | | | | |
|---|---|---|---|---|---|---|---|---|---|---|---|
| Ingredient | 1 | 2 | 3 | 4 | 5 | 6 | 7 | 8 | 9 | 10 | 11 |
| 4033 | | | | | | | 60 | | | | 56 |
| JL-007 | 55 | 60 | 60 | 60 | | 55 | | | 60 | 56 | |
| JL-014 | | | | | 55 | | | 60 | | | |
| Oil | 15 | 20 | 20 | 16 | 15 | 15 | 20 | 20 | 20 | 31 | 31 |
| Regalrez 1126 | 15 | 10 | 15 | 16 | 15 | | 10 | 10 | | | |
| Regalite 1125 | | | | | | 15 | | | 10 | | |
| PS 3190 | 15 | 10 | 5 | 8 | 15 | 15 | 10 | 10 | 10 | 13 | 13 |
| AO | 0.05 | | | | 0.05 | 0.05 | | | | 0.1 | 0.1 | the samples formed from the JL-series of SEEPS block copolymers provide these desired properties.

Laminates were made using films formed from the SEEPS block copolymers indicated in Table 4. The weight percents of the individual film components are based on the total weight of the film and are also shown in Table 4. The films in are formed by extrusion on lab scale extrusion equipment with a temperature profile of between 180° C. at the first barrel stage and 215° C. at the extrusion die. The films have basis weights in the range of 130 to 140 gsm. A hot melt adhesive (e.g., product code 2031 available from Bostik) is applied in a spiral pattern to sheets of release paper having sufficient dimensions to cover the nonwoven and form the laminate samples described below. The adhesive is applied at a basis weight of 6.2 gsm via a spray melt process. The adhesive is transferred from the release paper to a first nonwoven material (16.5 gsm SMS nonwoven available from Fibertex under product no. ESM0337) by placing the nonwoven on the release paper and lightly pressing down on the nonwoven with moderate hand pressure to ensure good contact between the nonwoven and adhesive. The nonwoven is then carefully peeled from the release paper to transfer the adhesive from the release paper to the nonwoven. This process is repeated so that the adhesive is applied to the same side of the nonwoven twice. After removing the nonwoven from the release paper a second time, the adhesive containing side of the nonwoven is then placed on the film to adhere the nonwoven to the film. The process of applying adhesive to a nonwoven is then repeated on a second, identical nonwoven material. The second nonwoven material is then adhered to the opposite side of the film (i.e., one layer of nonwoven for each of the opposing surfaces of the film). Ensure that the nonwoven and film machine directions are coincident. The laminates are trimmed to a length and width of 100 mm and 50.8 mm, respectively. All samples are than stacked in the same stack and subjected to a pressure of 20 kPa for three seconds. Each laminate is then subjected to an activation process where the laminate is activated to an 8 mm depth-of-engagement on 200-pitch ring roll plates, wherein the teeth have a tip radius of 120 µm. In this way, 250% engineering strain is applied to the laminate in 0.2 seconds along the machine direction of the laminate to each span of material positioned between each pair of teeth. This causes permanent deformation of the nonwoven. Thus, the elastomeric film is able to stretch with substantially reduced mechanical interference from the nonwoven (relative to a non-activated laminate).

TABLE 4

| No. | Sample ID | S4033 | JL013 | PS 3190 | DRAKEOL 600 |
|---|---|---|---|---|---|
| 1 | grf410-17a | 0.56 | | 0.13 | 0.31 |
| 2 | grf410-17c | | 0.56 | 0.13 | 0.31 |

Table 5 illustrates the laminate integrity times and time-to-fail of the laminates from Table 4 when tested according to the Laminate Integrity Test.

TABLE 5

| No. | Sample ID | laminate integrity time (hr.) | Time-to-fail |
|---|---|---|---|
| 1 | GRF410-17a | 1.85 | 0.36 |
| 2 | GRF410-17c | 5.20 | 1.7 |

As can be seen from Table 5, Sample 2 exhibits a suitable laminate integrity time of greater than 2 hours. In contrast, Sample 1, which is provided as a comparative example, does not exhibit a suitable laminate integrity time of greater than 2 hours. Similarly, Sample 1 does not provide a suitable Time-to-fail of greater than 1 hour.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm." Additionally, properties described herein may include one or more ranges of values. It is to be understood that these ranges include every value within the range, even though the individual values in the range may not be expressly disclosed.

All documents cited in the Detailed Description of the Invention are, in relevant part, incorporated herein by reference; the citation of any document is not to be construed as an admission that it is prior art with respect to the present invention. To the extent that any meaning or definition of a term in this document conflicts with any meaning or definition of the same term in a document incorporated by reference, the meaning or definition assigned to that term in this document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. A multilayer laminate material, which resists the growth of a tear, hole, or aperture, the laminate comprising: at least one extensible nonwoven layer joined to at least one elastomeric film layer in a face-to-face relationship, the elastomeric film layer having a $T_m$ of between about 10° C. and about 20° C. and a laminate integrity time of greater than about 2 hours according to the Laminate Integrity Test wherein the elastomeric film layer comprises a SEEPS elastomeric block copolymer.

2. The multilayer laminate of claim 1, wherein the laminate integrity time is greater than about 5 hours.

3. The multilayer laminate of claim 1, wherein the laminate integrity time is greater than about 20 hours.

4. The multilayer laminate of claim 1, wherein the elastomeric film layer has a time-to-fail value of greater than about 1 hour.

5. The multilayer laminate of claim 4, wherein the time-to-fail is greater than about 12 hours.

6. The multilayer laminate of claim 4, wherein the time-to-fail is greater than about 24 hours.

7. The multilayer laminate of claim 1, wherein the elastomeric film layer has a thickness of between about 1 µm and about 1 mm.

8. The multilayer laminate of claim 1, wherein the elastomeric film layer has a basis weight of between about 20 and about 140 grams per square meter.

9. The multilayer laminate of claim 1, wherein the elastomeric film layer is sandwiched between two or more nonwoven layers.

10. The multilayer laminate of claim 1, wherein the nonwoven layer is plastically extensible and at least a portion of the nonwoven layer is activated.

11. The multilayer laminate of claim 1, wherein the laminate is breathable.

12. The multilayer laminate of claim 1, wherein the nonwoven layer is elastically extensible.

13. A multilayer, elastic laminate material that resists the growth of a tear, the laminate comprising: an elastomeric film layer sandwiched between two plastically extensible nonwoven layers, the nonwoven layers being adhesively joined to opposing sides of the film layer, the elastomeric film material comprising a SEEPS elastomeric block copolymer having a $T_m$ of between about 10° C. and 20° C., the laminate having a laminate integrity time of greater than 2 hours according to the Laminate Integrity Test.

14. The multilayer laminate of claim 13, wherein at least a portion of one of the nonwoven layers is activated.

15. The multilayer laminate of claim 13, wherein at least one of nonwoven layers is configured as a spunbond-meltblown-spunbond nonwoven layer.

16. The multilayer laminate of claim 13, wherein the laminate integrity time is greater than about 5 hours.

17. The multilayer laminate of claim 13, wherein the laminate integrity time is greater than 20 hours.

18. The multilayer laminate of claim 13, wherein the elastomeric film material has a time to break of at least about 1 hour.

19. The multilayer laminate of claim 13, wherein the laminate is incorporated into an absorbent article as a component selected from the group consisting of a topsheet, a backsheet, an outer cover, a cuff, a side panel, an ear, a fastener, and combinations of these.

* * * * *